United States Patent [19]

Ataka et al.

[11] Patent Number: 4,982,008
[45] Date of Patent: Jan. 1, 1991

[54] PROCESS FOR PREPARING P-BROMOPHENOXYACETALDEHYDE DIALKYLACETAL COMPOUNDS

[75] Inventors: Kikuo Ataka; Masahiko Kohno, both of Ube, Japan

[73] Assignees: Ube Industries, Ltd., Ube; Sankyo Co., Ltd., Tokyo, both of Japan

[21] Appl. No.: 397,995

[22] Filed: Aug. 23, 1989

[30] Foreign Application Priority Data

Aug. 30, 1988 [JP] Japan .................... 63-213637

[51] Int. Cl.$^5$ .......................... C07C 43/30
[52] U.S. Cl. .................................. 568/592
[58] Field of Search .......................... 568/592

[56] References Cited

U.S. PATENT DOCUMENTS 3,780,104 12/1973 Teach .
3,890,134 6/1975 Teach .
4,845,097 7/1989 Matsumoto et al. ........... 514/234.2

FOREIGN PATENT DOCUMENTS 59-36667 2/1984 Japan .
62-67 1/1987 Japan .

OTHER PUBLICATIONS

Niwa et al, Development of (Phenoxyphenoxy) and (Benzylphenoxy)allanaldoxime O-Ethers as Potent Insect Juvenile Hormone Mimics and Their Quantitative Structure-Activity Relationship, J. Agric. Food Chem., 1988, 36, pp. 378-384.

Primary Examiner—Bruce Gray
Attorney, Agent, or Firm—Frishauf, Holtz, Goodman & Woodward

[57] ABSTRACT

There is disclosed a process for preparing a p-bromophenoxyacetaldehyde dialkylacetal derivative represented by the formula:

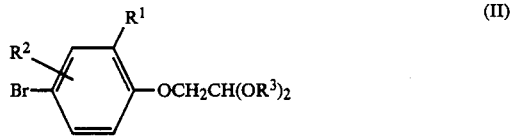

(II)

wherein $R^1$ and $R^2$ each represent a hydrogen atom or a lower alkyl group and $R^3$ represents an alkyl group having 1 to 6 carbon atoms, which comprises reacting a bromine to a phenoxyacetaldehyde dialkylacetal represented by the formula:

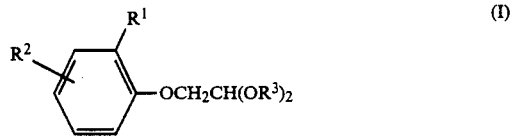

(I)

wherein $R^1$, $R^2$ and $R^3$ have the same meanings as defined above, and then the reaction mixture is treated with an alkali metal hydroxide or alcoholate dissolved in an alcohol represented by the formula:

$R^3OH$ wherein $R^3$ has the same meaning as defined above.

22 Claims, No Drawings

PROCESS FOR PREPARING P-BROMOPHENOXYACETALDEHYDE DIALKYLACETAL COMPOUNDS

BACKGROUND OF THE INVENTION

This invention relates to an improved process for preparing p-bromophenoxyacetaldehyde dialkylacetal derivatives.

The acetals are useful for synthetic intermediate of a substituted phenoxyalkylaminopyrimidine derivative (for example, Japanese Provisional Patent Publications No. 36667/1984 and No. 67/1987) which shows potent activity as an antiacaricide.

p-Bromophenoxyacetaldehyde dialkylacetal derivatives have heretofore been prepared by reacting p-bromophenols and chloroacetaldehyde dialkylacetals in the presence of a base (J. Argic. Food Chem., vol 36, p. 378 (1988), French Pat. No. 1,537,206 and Japanese Provisional Patent Publication No. 313743/1988). However, this method has disadvantages that (1) ortho-isomer and dibromo compound are formed with amounts of 20 to 30% when phenols being brominated and (2) the reaction rate is extremely slow.

The former disadvantage can be overcome only by recrystallization to obtain the pure para-isomer. Besides, in order to overcome the latter disadvantage of reaction rate, bromoaccetaldehyde dialkylacetals which are expensive and hardly obtainable in industry must be used in place of cheap chloroacetaldehyde dialkylacetal, and also as a solvent, amides such as dimethylformamide, which are easily decomposable should be used. The acetal substituent is generally extremely weak to acid, and it is decomposed in the condition of forming hydrogen bromide, so that a novel method which is to be replaced with the conventional method has been desired.

SUMMARY OF THE INVENTION

The present inventors have found that after reacting bromine with phenoxyacetaldehyde dialkylacetals, a specific treatment is effected to the reaction mixture whereby bromination reaction proceeds smoothly and surprisingly the aimed compound can be obtained with extremely high yield and selectively without forming by-products such as ortho-isomer and dibromo compound to accomplish the present invention.

That is, the present invention is a process for preparing a p-bromophenoxyacetaldehyde dialkylacetal derivative represented by the formula:

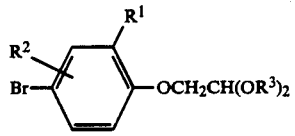
(II)

wherein $R^1$ and $R^2$ each represent a hydrogen atom or a lower alkyl group and $R^3$ represents an alkyl group having 1 to 6 carbon atoms,
which comprises reacting bromine with a phenoxyacetaldehyde dialkylacetal represented by the formula:

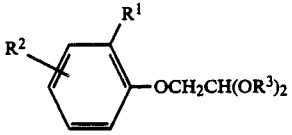
(I)

wherein $R^1$, $R^2$ and $R^3$ have the same meanings as defined above,
and then the reaction mixture is treated with an alkali metal hydroxide or alcoholate (or alkoxide) dissolved in an alcohol represented by the formula:

$R^3OH$ wherein $R^3$ has the same meaning as defined above.

DESCRIPTION OF THE PREFERRED EMBODIMENTS

The starting compound of the formula (I) can be obtained with a similar method as disclosed in Japanese Patent Publication No. 50466/1987 by reacting phenols and chloroacetaldehyde dialkylacetal in the presence of a base without using a specific solvent.

Japanese Patent Publication No. 50466/1987 describes the following scheme:

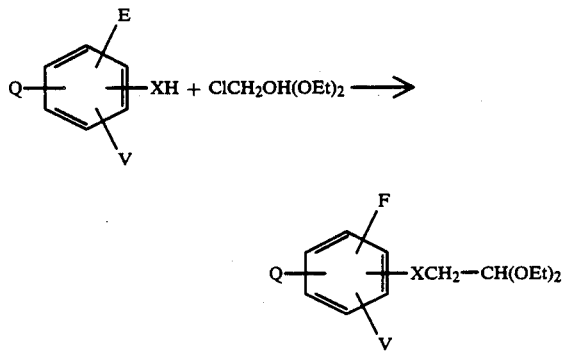

wherein Q is $C_1$ to $C_6$ alkoxy or $C_1$ to $C_6$ alkylthio and E and V are each preferbly hydrogen, halogen, nitro, $C_1$ to $C_6$ alkyl and $C_1$ to $C_6$ haloalkyl.

Furthermore, the following Example is described in Japanese Patent Publication No. 50466/1987:

Preparation of Methyl 2-[4-(Pyrimidyl-5-oxy)phenoxy]-propionate (93)

Potassium hydroxide pellets (22.4 g) and molten p-methoxyphenol (50 g) were heated with stirring to a temperature in the range from 90° to 100° C. until a clear solution was obtained. Chloroacetaldehyde diethylacetal (120 g) was added at such a rate to maintain the temperature in the range from 90° to 100° C. and after stirring for a further 15 minutes water was removed from the flask as an azeotrope with chloroacetaldehyde diethylacetal, the water and acetal were separated and the acetal was returned to the reaction mixture. Azeotropic distillation was continued until the temperature of the vapour reached 140°-150° C. and then the reaction mixture was heated under reflux for a further 6 hr. Water (200 ml) was added to the cooled mixture which was then extracted with chloroform (2×200 ml). The chloroform extracts were washed with aqueous 2N sodium hydroxide (100 ml) to remove unreacted phenols and the chloroform layer was dried over Na₂SO₄ and the solvent removed by distillation under reduced pressure. The crude product was distilled under reduced pressure to give, as a third fraction, p-methoxyphenoxyacetaldehyde diethyl acetal (45.6 g) of b.p. 180°–194° C. at 44 mm the product being characterized by p.m.r. spectroscopy.

A reaction solvent to be used in the present invention may preferably include an alcohol (R³OH) which is the same with an alcohol which constitutes alkylacetal, or alkane chlorides such as methylene chloride, dichloroethane, trichloroethane, etc. An amount of bromine is preferably 1.0 to 1.3 mole based on the starting compound of the formula (I). The reaction can be carried out at a reaction temperature in the range of −10° to 50° C., but preferably in the range of 0° to 10° C. The reaction can be carried out with a solution containing the compound of the formula (I) of 1 to 50% by weight in a reaction concentration, but generally preferably 5 to 30% by weight. A time required for dropwise addition of bromine is 1 to 5 hours, and the reaction is completed within one hour after dropwise addition of bromine. After completion of the reaction, the reaction mixture as it were or partially or completely removed the reaction solvent under reduced pressure (200 to 20 mmHg, 40° C. or lower) is added dropwise to an alcoholic solution of an alkali metal hydroxide dissolved in an alcohol of the formula R³OH while maintaining a temperature of the reaction mixture to 30° C. or lower. As the alkali metal hydroxide, it may preferably include sodium hydroxide, potassium hydroxide, etc. An amount of the alkali metal hydroxide or alcoholate (alkoxide) is 0.5 to 2.0-fold moles of the used bromine. An alkali metal alcoholate is also used as an alcoholic solution of the formula R³OH. As the alkali metal alkoxide, it may preferably include lithium alkoxide, sodium alkoxide, potassium alkoxide, etc.

After completion of the above treatment, the solvent was removed under reduced pressure and after removing an inorganic salt formed with filtration, washing, etc., the compound of the formula (II) can be obtained by distillation under reduced pressure, recrystallization, etc.

As the p-bromophenoxyacetaldehyde dialkylacetals (II), there may be mentioned
1-bromo-4-(2,2-diethoxyethoxy)benzene,
1-bromo-4-(2,2-dimethoxyethoxy)benzene,
1-bromo-4-(2,2-diethoxyethoxy)-3-methylbenzene,
1-bromo-4-(2,2-dimethoxyethoxy)-3-methylbenzene,
1-bromo-4-(2,2-diethoxyethoxy)-3-ethylbenzene,
1-bromo-4-(2,2-dimethoxyethoxy)-3-ethylbenzene,
1-bromo-4-(2,2-diethoxyethoxy)-2,3-dimethylbenzene,
1-bromo-4-(2,2-dimethoxyethoxy)-2,3-dimethylbenzene,
1-bromo-4-(2,2-diethoxyethoxy)-2,5-dimethylbenzene,
1-bromo-4-(2,2-dimethoxyethoxy)-2,5-dimethylbenzene,
1-bromo-4-(2,2-diethoxyethoxy)-3,5-dimethylbenzene,
1-bromo-4-(2,2-dimethoxyethoxy)-3,5-dimethylbenzene, etc.

EXAMPLES

In the following, the present invention will be explained in more detail by referring to Examples.

Example 1

Bromine (140 g) was added dropwise to a 760 ml of dichloroethane solution containing 180 g of 1-(2,2-dimethoxyethoxy)-2,3-dimethylbenzene while stirring and cooling (ice bath) and maintaining the temperature of the reaction mixture not exceeding 10° C. After stirring for 30 minutes after completion of the addition, the reaction mixture was condensed under reduced pressure (a temperature of 40° C. or lower). The condensate was added dropwise in a solution comprising 37 g of sodium hydroxide dissolved in 185 g of methanol while stirring. Stirring was continued for one hour after completion of the addition, methanol was removed under reduced pressure, and 30 ml of dichloroethane and 570 ml of water were added to the residue and then the mixture was separated with each other. The organic layer was condensed under reduced pressure, a resulting brownish oil was distilled under reduced pressure to give 228 g of 1-bromo-4-(2,2-dimethoxyethoxy)-2,3-dimethylbenzene. Boiling point: 128° to 131° C./0.5 mmHg; Melting point: 40° to 41° C.; and Yield: 92%.

Example 2

In the same manner as in Example 1 except for replacing a methanol solution of sodium hydroxide with 180 ml of methanol solution containing 28% of sodium methylate, the reaction was carried out as in Example 1. As the result, 1-bromo-4-(2,2-dimethoxyethoxy)-2,3-dimethylbenzene was obtained with a yield of 93%.

Example 3

In the same manner as in Example 1 except for replacing a reaction solvent for bromination of dichloroethane with methanol, the reaction was carried out as in Example 1. Yield: 93%.

Example 4

In the same manner as in Example 1 except for replacing 1-(2,2-dimethoxyethoxy)-2,3-dimethylbenzene with 2,2-diethoxyethoxybenzene, the reaction was carried out as in Example 1 (with 1/50 scale of Example 1) to give 1-bromo-4-(2,2-diethoxyethoxy)benzene (Boiling point: 123° to 127° C./2 mmHg) with a yield of 89%.

Example 5

In the same manner as in Example 1 except for replacing 1-(2,2-dimethoxyethoxy)-2,3-dimethylbenzene with 1-(2,2-diethoxyethoxy)-2-ethylbenzene, the reaction was carried out as in Example 1 (with 1/50 scale of Example 1) to give 1-bromo-4-(2,2-diethoxyethoxy)-3-ethylbenzene (Boiling point: 180° to 185° C./7 mmHg) with a yield of 90%.

Example 6

In the same manner as in Example 1 except for replacing 1-(2,2-dimethoxyethoxy)-2,3-dimethylbenzene with 1-(2,2-dimethoxyethoxy)-2,5-dimethylbenzene, the reaction was carried out as in Example 1 to give 1-bromo-4-(2,2-dimethoxyethoxy)-2,5-dimethylbenzene (Boiling point: 118° to 120° C./2.5 mmHg) with a yield of 91%.

Example 7

In the same manner as in Example 1 except for replacing 1-(2,2-dimethoxyethoxy)-2,3-dimethylbenzene with 1-(2,2-diethoxyethoxy)-2,6-dimethylbenzene, the reaction was carried out as in Example 1 to give 1-bromo-4-

(2,2-diethoxyethoxy)-3,5-dimethylbenzene (Boiling point: 138° to 145° C./4 mmHg) with a yield of 96%.

According to the present invention, the aimed p-bromophenoxyacetaldehyde dialkylacetal can be obtained with high yield and high purity and forming substantially no by-products such as ortho-isomer and dibromo compounds.

We claim:

1. A process for preparing a p-bromophenoxyacetaldehyde dialkylacetal compound represented by the formula:

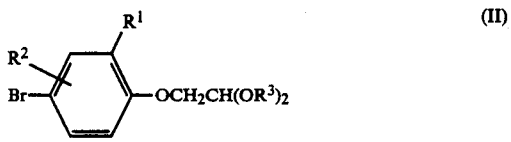
(II)

wherein $R^1$ and $R^2$ each represent a hydrogen atom or a lower alkyl group and $R^3$ represents an alkyl group having 1 to 6 carbon atoms,
which comprises reacting bromine with a phenoxyacetaldehyde dialkylacetal represented by the formula:

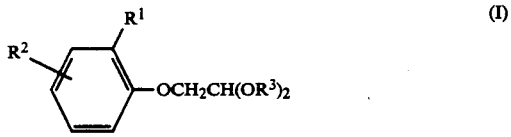
(I)

wherein $R^1$, $R^2$ and $R^3$ have the same meanings as defined above,
and then treating the reaction mixture with an alkali metal hydroxide or alcoholate dissolved in an alcohol represented by the formula:

$R^3OH$ wherein $R^3$ has the same meaning as defined above.

2. A process for preparing a p-bromophenoxyacetaldehyde dialkylacetal compound according to claim 1, wherein the reaction is carried out in the presence of a solvent.

3. A process for preparing a p-bromophenoxyacetaldehyde dialkylacetal compound according to claim 2, wherein the solvent is an alcohol represented by the formula $R^3OH$ wherein $R^3$ has the same meaning as defined in claim 1; or is an alkane chloride selected from the group consisting of methylene chloride, dichloroethane and trichloroethane.

4. A process for preparing a p-bromophenoxyacetaldehyde dialkylacetal compound according to claim 1, wherein the amount of bromine provided for said reaction is 1.0 to 1.3 mols per mol of phenoxyacetaldehyde dialkylacetal of the formula (I) which is reacted therewith.

5. A process for preparing a p-bromophenoxyacetaldehyde dialkylacetal compound according to claim 4, wherein the bromine is added dropwise to a solution of phenoxyacetaldehyde dialkylacetal of the formula (I).

6. A process for preparing a p-bromophenoxyacetaldehyde dialkylacetal compound according to claim 5, wherein said dropwise addition is carried out within 1 to 5 hours.

7. A process for preparing a p-bromophenoxyacetaldehyde dialkylacetal compound according to claim 1, wherein the reaction with bromine is carried out at a temperature of −10° to 50° C.

8. A process for preparing a p-bromophenoxyacetaldehyde dialkylacetal compound according to claim 7, wherein the reaction is carried out at a temperature of 0° to 10° C.

9. A process for preparing a p-bromophenoxyacetaldehyde dialkylacetal compound according to claim 1, wherein the concentration of the phenoxyacetadehyde dialkylacetal of the formula (I) in the reaction mixture is 1 to 50% by weight.

10. A process for preparing a p-bromophenoxyacetaldehyde dialkylacetal compound according to claim 9, wherein the concentration of the phenoxyacetaldehyde dialkylacetal of the formula (I) is 5 to 30% by weight.

11. A process for preparing a p-bromophenoxyacetaldehyde dialkylacetal compound according to claim 2, wherein treatment with an alkali metal hydroxide or the alcoholate dissolved in alcohol is carried out by dropwise adding the reaction mixture in an alcoholic solution thereto.

12. A process for preparing a p-bromophenoxyacetaldehyde dialkylacetal compound according to claim 11, wherein the dropwise addition of the reaction mixture is carried out at a temperature of 30° C. or lower.

13. A process for preparing a p-bromophenoxyacetaldehyde dialkylacetal compound according to claim 1, wherein the alkali metal hydroxide is sodium hydroxide or potassium hydroxide.

14. A process for preparing a p-bromophenoxyacetaldehyde dialkylacetal compound according to claim 1, wherein the alcoholate is lithium alkoxide, sodium alkoxide or potassium alkoxide.

15. A process for preparing a p-bromophenoxyacetaldehyde dialkylacetal compound according to claim 1, wherein the amount of the alkali metal hydroxide or alcoholate is 0.5 to 2.0 mol per mol bromine used.

16. A process for preparing a p-bromophenoxyacetaldehyde dialkylacetal compound according to claim 1, wherein the process further comprises removing an inorganic salt formed and then purifying said p-bromophenoxyacetaldehyde dialkylacetal compound by distillation under reduced pressure or by recrystallization.

17. A process for preparing a p-bromophenoxyacetaldehyde dialkylacetal derivative according to claim 1, wherein the process comprises adding dropwise bromine to the phenoxyacetaldehyde dialkylacetal dissolved in a solvent a concentration of which is 1 to 50% by weight, with an amount of 1.0 to 1.3 moles at a temperature of −10° to 50° C.; and then the reaction mixture is added dropwise to the alkali metal hydroxide or alcoholate dissolved in the alcohol an amount of which is 0.5 to 2.0-fold moles based on used bromine, at a temperature of 30° C. or lower.

18. A process for preparing a p-bromophenoxyacetaldehyde dialkylacetal derivative according to claim 1, wherein the process comprises adding dropwise bromine to the phenoxyacetaldehyde dialkylacetal dissolved in a solvent a concentration of which is 5 to 30% by weight, with an amount of 1.0 to 1.3 moles at a temperature of 0° to 10° C.; and then the reaction mixture is added dropwise to the alkali metal hydroxide or alcoholate dissolved in the alcohol an amount of which is 0.5 to 2.0-fold moles based on used bromine, at a temperature of 30° C. or lower.

19. A process for preparing a p-bromophenoxyacetaldehyde dialkylacetal compound according to claim 1, wherein the p-bromophenoxyacetaldehyde dialkylacetal of the formula (II) is selected from
1-bromo-4-(2,2-diethoxyethoxy)benzene,
1-bromo-4-(2,2-dimethoxyethoxy)benzene,
1-bromo-4-(2,2-diethoxyethoxy)-3-methylbenzene,
1-bromo-4-(2,2-dimethoxyethoxy)-3-methylbenzene,
1-bromo-4-(2,2-diethoxyethoxy)-3-ethylbenzene,
1-bromo-4-(2,2-dimethoxyethoxy)-3-ethylbenzene,
1-bromo-4-(2,2-diethoxyethoxy)-2,3-dimethylbenzene,
1-bromo-4-(2,2-dimethoxyethoxy)-2,3-dimethylbenzene,
1-bromo-4-(2,2-diethoxyethoxy)-2,5-dimethylbenzene,
1-bromo-4-(2,2-dimethoxyethoxy)-2,5-dimethylbenzene,
1-bromo-4-(2,2-diethoxyethoxy)-3,5-dimethylbenzene and
1-bromo-4-(2,2-dimethoxyethoxy)-3,5-dimethylbenzene.

20. A process for preparing a p-bromophenoxyacetaldehyde dialkylacetal compound according to claim 1, wherein the process comprises dropwise adding bromine, over a period of from 1 to 5 hours, to a solution of said phenoxyacetaldehyde dialkylacetal dissolved in a solvent, the concentration of said solvent being between 1.0 and 50% by weight of the total weight of solvent and dialkylacetal, the amount of bromine added being between 1.0 to 3.0 mols per mol of dialkylacetal in said solution and with said solution being held at a temperature between $-10°$ and 50° C., the reaction of said dialkylacetal with bromine being continued for up to about 1 hour after said bromine has been completely added, said reaction then being followed by the steps of condensing the brominated reaction mixture under a reduced pressure, at a temperature of 40° C. or lower, with the condensed mixture then being dropwise added to the alcohol solution of said alkali metal hydroxide or alcoholate, said alcohol solution containing 0.5 to 2.0 mols of hydroxide or alcoholate per mol of bromine added and being at a temperature of 30° C. or lower, followed by recovering the brominated dialkylacetal compound therefrom by extracting said compound from said solution with a mixture of water and a chlorinated ethane, separating the extracted mixture from the remainder of the solution and, under reduced pressure, distilling off the extractant mixture.

21. The process according to claim 20 wherein the solvent is 5 to 30% of the total weight and the reaction is conducted at a temperature between 0° and 10° C.

22. A process for preparing a p-bromophenoxyacetaldehyde dialkylacetal compound according to claim 21, wherein the p-bromophenoxyacetaldehyde dialkylacetal of the formula (II) is selected from
1-bromo-4-(2,2-diethoxyethoxy)benzene,
1-bromo-4-(2,2-dimethoxyethoxy)benzene,
1-bromo-4-(2,2-diethoxyethoxy)-3-methylbenzene,
1-bromo-4-(2,2-dimethoxyethoxy)-3-methylbenzene,
1-bromo-4-(2,2-diethoxyethoxy)-3-ethylbenzene,
1-bromo-4-(2,2-dimethoxyethoxy-3-ethylbenzene,
1-bromo-4-(2,2-diethoxyethoxy-2,3-dimethylbenzene,
1-bromo-4-(2,2-dimethoxyethoxy)-2,3-dimethylbenzene,
1-bromo-4-(2,2-diethoxyethoxy)-2,5-dimethylbenzene,
1-bromo-4-(2,2-dimethoxyethoxy)-2,5-dimethylbenzene,
1-bromo-4-(2,2-diethoxyethoxy)-3,5-dimethylbenzene and
1-bromo-4-(2,2-dimethoxyethoxy)-3,5-dimethylbenzene.

* * * * *